United States Patent
Roth et al.

(10) Patent No.: US 8,704,025 B2
(45) Date of Patent: Apr. 22, 2014

(54) MOLECULAR SIEVE COMPOSITION EMM-12, A METHOD OF MAKING AND A PROCESS OF USING THE SAME

(75) Inventors: Wieslaw J. Roth, Sewell, NJ (US); Douglas L. Dorset, Milford, NJ (US); Gordon J. Kennedy, Washington, NJ (US); Thomas Yorke, Toms River, NJ (US); Terry Eugene Helton, Bethlehem, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 461 days.

(21) Appl. No.: 12/999,585

(22) PCT Filed: Jul. 15, 2009

(86) PCT No.: PCT/US2009/050729
§ 371 (c)(1),
(2), (4) Date: Mar. 25, 2011

(87) PCT Pub. No.: WO2010/021795
PCT Pub. Date: Feb. 25, 2010

(65) Prior Publication Data
US 2011/0166401 A1    Jul. 7, 2011

Related U.S. Application Data

(60) Provisional application No. 61/084,166, filed on Jul. 28, 2008.

(30) Foreign Application Priority Data

Oct. 2, 2008 (EP) .................................... 08165750

(51) Int. Cl.
*C07C 2/68* (2006.01)
(52) U.S. Cl.
USPC ............ 585/467; 423/718; 423/700; 423/701

(58) Field of Classification Search
USPC .......................................... 585/467; 423/718
See application file for complete search history.

(56) References Cited

U.S. PATENT DOCUMENTS

| 3,751,504 A | 8/1973 | Keown et al. |
| 4,016,218 A | 4/1977 | Haag et al. |

(Continued)

FOREIGN PATENT DOCUMENTS

| CN | 100546910 | 10/2009 |
| EP | 0 293 032 | 11/1988 |

(Continued)

OTHER PUBLICATIONS

Wu et al., "Methodology for Synthesizing Crystalline Metallosilicates with Expanded Pore Windows Through Molecular Alkoxysilylation of Zeolitic Lamellar Precursors" in J. Am. Chem. Soc. 2008, 130, 8178-8187, published on-line Jun. 4, 2008. http://pubs.acs.org/doi/pdf/10.1021/ja0758739.*

(Continued)

*Primary Examiner* — Walter D Griffin
*Assistant Examiner* — Jelitza Perez
(74) *Attorney, Agent, or Firm* — Darryl M. Tyus

(57) ABSTRACT

This disclosure relates to an EMM-12 molecular sieve having, in its as-synthesized form and in calcined form, an X-ray diffraction pattern including peaks having a d-spacing maximum in the range of 14.17 to 12.57 Angstroms, a d-spacing maximum in the range of 12.1 to 12.56 Angstroms, and non-discrete scattering between about 8.85 to 11.05 Angstroms or exhibit a valley in between the peaks having a d-spacing maximum in the range of 10.14 to 12.0 Angstroms and a d-spacing maximum in the range from 8.66 to 10.13 Angstroms with measured intensity corrected for background at the lowest point being not less than 50% of the point at the same XRD d-spacing on the line connecting maxima in the range of 10.14 to 12.0 Angstroms and in the range from 8.66 to 10.13 Angstroms.

15 Claims, 6 Drawing Sheets

(56) References Cited

U.S. PATENT DOCUMENTS

| | | | |
|---|---|---|---|
| 4,439,409 | A | 3/1984 | Puppe et al. |
| 4,547,605 | A | 10/1985 | Kresge et al. |
| 4,826,667 | A | 5/1989 | Zones et al. |
| 4,891,458 | A | 1/1990 | Innes et al. |
| 4,954,325 | A | 9/1990 | Rubin et al. |
| 4,954,663 | A | 9/1990 | Marler et al. |
| 4,956,514 | A | 9/1990 | Chu |
| 4,962,239 | A | 10/1990 | Bell et al. |
| 4,962,250 | A | 10/1990 | Dessau et al. |
| 4,962,255 | A | 10/1990 | Fraenkel et al. |
| 4,962,256 | A | 10/1990 | Le et al. |
| 4,962,257 | A | 10/1990 | Absil et al. |
| 4,968,402 | A | 11/1990 | Kirker et al. |
| 4,973,784 | A | 11/1990 | Han et al. |
| 4,982,033 | A | 1/1991 | Chu et al. |
| 4,982,040 | A | 1/1991 | Angevine et al. |
| 4,983,276 | A | 1/1991 | Absil et al. |
| 4,986,894 | A | 1/1991 | Keville et al. |
| 4,992,606 | A | 2/1991 | Kushnerick et al. |
| 4,992,611 | A | 2/1991 | Morrison |
| 4,992,615 | A | 2/1991 | Huss, Jr. et al. |
| 5,000,839 | A | 3/1991 | Kirker et al. |
| 5,001,283 | A | 3/1991 | Altman et al. |
| 5,001,295 | A | 3/1991 | Angevine et al. |
| 5,001,296 | A | 3/1991 | Howley et al. |
| 5,012,033 | A | 4/1991 | Child et al. |
| 5,013,422 | A | 5/1991 | Absil et al. |
| 5,019,664 | A | 5/1991 | Del Rossi et al. |
| 5,019,665 | A | 5/1991 | Partridge et al. |
| 5,019,670 | A | 5/1991 | Le et al. |
| 5,236,575 | A | 8/1993 | Bennett et al. |
| 5,250,277 | A | 10/1993 | Kresge et al. |
| 5,334,795 | A | 8/1994 | Chu et al. |
| 5,362,697 | A | 11/1994 | Fung et al. |
| 5,557,024 | A | 9/1996 | Cheng et al. |
| 6,077,498 | A | 6/2000 | Diaz Cabanas et al. |
| 6,231,751 | B1 * | 5/2001 | Canos et al. ............ 208/120.01 |
| 6,936,744 | B1 | 8/2005 | Cheng et al. |
| 6,984,764 | B1 | 1/2006 | Roth et al. |
| 2004/0092757 | A1 * | 5/2004 | Oguchi et al. ................ 549/533 |
| 2005/0158238 | A1 | 7/2005 | Tatsumi et al. |
| 2008/0027259 | A1 * | 1/2008 | Roth et al. .................... 585/475 |
| 2008/0045768 | A1 | 2/2008 | Roth et al. |

FOREIGN PATENT DOCUMENTS

| | | |
|---|---|---|
| JP | 2008-162846 | 7/2008 |
| WO | WO 97/17290 | 5/1997 |
| WO | WO 2005/003031 | 1/2005 |
| WO | WO 2005/090323 | 9/2005 |
| WO | WO 2005/118476 | 12/2005 |
| WO | WO 2006/015824 | 2/2006 |
| WO | WO 2006/015825 | 2/2006 |
| WO | WO 2006/015826 | 2/2006 |
| WO | WO 2008/013644 | 1/2008 |
| WO | WO 2008/016477 | 2/2008 |
| WO | WO 2010/014405 | 2/2010 |
| WO | WO 2010/014406 | 2/2010 |

OTHER PUBLICATIONS

W. Meier et al., "*Atlas of Zeolite Framework Types*", Elsevier, Fifth Edition, 2001.

W. Fan et al., "*A Titanosilicate That is Structurally Analogous to an MWW-Type Lamellar Precursor*", Angew. Chem. Int. Ed., 2004, vol. 43, pp. 236-240.

W. Fan et al., "*Synthesis and Catalytic Properties of a New Titanosilicate Molecular Sieve With the Structure Analogous to MWW-Type Lamellar Precursor*", Journal of Catalysis, 2006, vol. 243, pp. 183-191.

J. Ruan et al., "*Structure Elucidation of the Highly Active Titanosilicate Catalyst Ti-YNU-1*", Angew. Chem. Int. Ed., 2005, vol. 44, pp. 6719-6723.

J. Raun et al., "*Structure Investigation of Novel 3-D Crystalline Silicates From Layered Precursors*," 15 IZC Conference, Beijing, Book of Abstracts (2007).

S-Y. Kim et al., "*Structural Evolution of B-MCM-36 and B-ITQ-2 From B-MCM-22*", Bull. Korean Chem. Soc., 2006, vol. 27, No. 10, pp. 1693-1696.

S. Lawton et al., "*Zeolite MCM-49: A Three-Dimensional MCM-22 Analogue Synthesized by In Situ Crystallization*", J. Phys. Chem., 1996, vol. 100, No. 9, pp. 3788-3798.

S. Maheshwari et al., "*Layer Structure Preservation During Swelling, Pillaring, and Exfoliation of a Zeolite Precursor*", J. Am. Chem. Soc., 2008, vol. 130, No. 4, pp. 1507-1516.

Z. Liu et al., "*Static synthesis of high-quality MCM-22 zeolite with high $SiO_2/Al_2O_3$ ratio,* " Chinese Science Bulletin, vol. 49, No. 6, pp. 556-561, 2004.

P. Wu et al., "*Methodology for Synthesizing Crystalline Metallosilicates with Expanded Pore Windows Through Molecular Alkoxysilylation of Zeolitic Lamellar Precursors,*" J. Am. Chem. Soc., 2008, vol. 130, No. 26, pp. 8178-8187.

"*Periodic Table of the Elements*", Chemical and Engineering News, 1985, vol. 63, No. 5, p. 27.

Kim et al., "*Ti-MCM-36: a new mesoporous epoxidation catalyst*", Catalysts Letters, vol. 113, Nos. 3-4, Feb. 2007.

* cited by examiner

MOLECULAR SIEVE COMPOSITION EMM-12, A METHOD OF MAKING AND A PROCESS OF USING THE SAME

CROSS-REFERENCE TO RELATED APPLICATIONS

This application is a 371 National Stage Application of International Application No. PCT/US2009/050729, filed Jul. 15, 2009, which claims the benefit of U.S. Provisional Application 61/084,166, filed Jul. 28, 2008, all of which are incorporated herein by reference in their entirety.

FIELD OF THE INVENTION

The present disclosure relates to a novel molecular sieve composition designated as EMM-12, a method of making and a process of using the same. In particular, this disclosure relates to a novel molecular sieve composition designated as EMM-12 which is an MCM-22 family material having unique XRD features.

BACKGROUND OF THIS DISCLOSURE

Molecular sieve materials, both natural and synthetic, have been demonstrated in the past to have catalytic properties for various types of hydrocarbon conversion. Molecular sieves that find application in catalysis include any of the naturally occurring or synthetic crystalline molecular sieves. Examples of these zeolites include large pore zeolites, intermediate pore size zeolites, and small pore zeolites. These zeolites and their isotypes are described in "Atlas of Zeolite Framework Types", eds. W. H. Meier, D. H. Olson and Ch. Baerlocher, Elsevier, Fifth Edition, 2001, which is hereby incorporated by reference. A large pore zeolite generally has a pore size of at least about 7 Å and includes LTL, VFI, MAZ, FAU, OFF, *BEA, and MOR framework type zeolites (IUPAC Commission of Zeolite Nomenclature). Examples of large pore zeolites include mazzite, offretite, zeolite L, VPI-5, zeolite Y, zeolite X, omega, and Beta. An intermediate pore size zeolite generally has a pore size from about 5 Å to less than about 7 Å and includes, for example, MFI, MEL, EUO, MTT, MFS, AEL, AFO, HEU, FER, MWW, and TON framework type zeolites (IUPAC Commission of Zeolite Nomenclature). Examples of intermediate pore size zeolites include ZSM-5, ZSM-11, ZSM-22, MCM-22, silicalite 1, and silicalite 2. A small pore size zeolite has a pore size from about 3 Å to less than about 5.0 Å and includes, for example, CHA, ERI, KFI, LEV, SOD, and LTA framework type zeolites (IUPAC Commission of Zeolite Nomenclature). Examples of small pore zeolites include ZK-4, ZSM-2, SAPO-34, SAPO-35, ZK-14, SAPO-42, ZK-21, ZK-22, ZK-5, ZK-20, zeolite A, chabazite, zeolite T, gmelinite, ALPO-17, and clinoptilolite.

U.S. Pat. No. 4,439,409 refers to a crystalline molecular sieve composition of matter named PSH-3 and its synthesis from a reaction mixture for hydrothermal reaction containing hexamethyleneimine, an organic compound which acts as directing agent for synthesis of the MCM-56 (U.S. Pat. No. 5,362,697). Hexamethyleneimine is also taught for use in synthesis of crystalline molecular sieves MCM-22 (U.S. Pat. No. 4,954,325) and MCM-49 (U.S. Pat. No. 5,236,575). A molecular sieve composition of matter referred to as zeolite SSZ-25 (U.S. Pat. No. 4,826,667) is synthesized from a reaction mixture for hydrothermal reaction containing an adamantane quaternary ammonium ion. U.S. Pat. No. 6,077,498 refers to a crystalline molecular sieve composition of matter named ITQ-1 and its synthesis from a reaction mixture for hydrothermal reaction containing one or a plurality of organic additives.

U.S. patent application Ser. No. 11/823,129 discloses a molecular sieve composition designated as EMM-10-P, having, in its as-synthesized form, an X-ray diffraction pattern including d-spacing maxima at 13.18±0.25 and 12.33±0.23 Angstroms, wherein the peak intensity of the d-spacing maximum at 13.18±0.25 Angstroms is at least as great as 90% of the peak intensity of the d-spacing maximum at 12.33±0.23 Angstroms. U.S. patent application Ser. No. 11/824,742 discloses a molecular sieve composition designated as EMM-10, in its ammonium exchanged form or in its calcined form, comprising unit cells with MWW topology, said crystalline molecular sieve is characterized by diffraction streaking from the unit cell arrangement in the c direction. The crystalline molecular sieve is further characterized by the arced hk0 patterns of electron diffraction pattern. The crystalline molecular sieve is further characterized by the streaks in the electron diffraction pattern along the c* direction. U.S. patent application Ser. No. 11/827,953 discloses a crystalline MCM-22 family molecular sieve having, in its as-synthesized form, an X-ray diffraction pattern including a peak at d-spacing maximum of 12.33±0.23 Angstroms, a distinguishable peak at a d-spacing maximum between 12.57 to about 14.17 Angstroms and a non-discrete peak at a d-spacing maximum between 8.8 to 11 Angstroms, wherein the peak intensity of the d-spacing maximum between 12.57 to about 14.17 Angstroms is less than 90% of the peak intensity of the d-spacing maximum at 12.33±0.23 Angstroms.

The term "MCM-22 family material" (or "material of the MCM-22 family" or "molecular sieve of the MCM-22 family"), as used herein, includes:

(i) molecular sieves made from a common first degree crystalline building block "unit cell having the MWW framework topology". A unit cell is a spatial arrangement of atoms which is tiled in three-dimensional space to describe the crystal as described in the "Atlas of Zeolite Framework Types", Fifth edition, 2001, the entire content of which is incorporated as reference;

(ii) molecular sieves made from a common second degree building block, a 2-dimensional tiling of such MWW framework type unit cells, forming a "monolayer of one unit cell thickness", preferably one c-unit cell thickness;

(iii) molecular sieves made from common second degree building blocks, "layers of one or more than one unit cell thickness", wherein the layer of more than one unit cell thickness is made from stacking, packing, or binding at least two monolayers of one unit cell thick of unit cells having the MWW framework topology. The stacking of such second degree building blocks can be in a regular fashion, an irregular fashion, a random fashion, or any combination thereof; or (iv) molecular sieves made by any regular or random 2-dimensional or 3-dimensional combination of unit cells having the MWW framework topology.

The MCM-22 family materials are characterized by having an X-ray diffraction pattern including d-spacing maxima at 12.4±0.25, 3.57±0.07 and 3.42±0.07 Angstroms (either calcined or as-synthesized). The MCM-22 family materials may also be characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize the molecular sieve are obtained by standard techniques using the K-alpha doublet of copper as the incident radiation and a diffractometer equipped with a scintillation counter and associated computer as the collection system. Materials belong to the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), ITQ-30 (described in International Patent Publication No. WO2005118476), MCM-36 (described in U.S. Pat. No. 5,250,277), MCM-49 (described in U.S. Pat. No. 5,236,575), MCM-56 (described in U.S. Pat. No. 5,362,697), EMM-10-P (described in U.S. patent application Ser. No. 11/823,129) and EMM-10 (described in U.S. patent application Ser. No. 11/824,742). The entire contents of the patents are incorporated herein by reference.

It is to be appreciated the MCM-22 family molecular sieves described above are distinguished from conventional large pore zeolite alkylation catalysts, such as mordenite, in that the MCM-22 materials have 12-ring surface pockets which do not communicate with the 10-ring internal pore system of the molecular sieve.

The zeolitic materials designated by the IZA-SC as being of the MWW topology are multi-layered materials which have two pore systems arising from the presence of both 10 and 12 membered rings. The Atlas of Zeolite Framework Types classes five differently named materials as having this same topology: MCM-22, ERB-1, ITQ-1, PSH-3, and SSZ-25.

The MCM-22 family molecular sieves have been found to be useful in a variety of hydrocarbon conversion processes. Examples of MCM-22 family molecular sieve are MCM-22, MCM-49, MCM-56, ITQ-1, PSH-3, SSZ-25, and ERB-1. Such molecular sieves are useful for alkylation of aromatic compounds. For example, U.S. Pat. No. 6,936,744 discloses a process for producing a monoalkylated aromatic compound, particularly cumene, comprising the step of contacting a polyalkylated aromatic compound with an alkylatable aromatic compound under at least partial liquid phase conditions and in the presence of a transalkylation catalyst to produce the monoalkylated aromatic compound, wherein the transalkylation catalyst comprises a mixture of at least two different crystalline molecular sieves, wherein each of the molecular sieves is selected from zeolite beta, zeolite Y, mordenite and a material having an X-ray diffraction pattern including d-spacing maxima at 12.4±0.25, 6.9±0.15, 3.57±0.07 and 3.42±0.07 Angstroms.

A report by J. Ruan, P. Wu, B. Slater, L. Wu, J. Xiao, Y. Liu, M. He, O. Terasaki at the 15 IZA Conference in Beijing in 2007 disclosed ISE-MWW and ISE-FER materials, the former made from MCM-22-P material as starting material. U.S. Patent Application Publication 2005/0158238 to Tatsumi et al. disclosed MWW type zeolite substance. U.S. Patent Application Publication 2004/0092757 to Oguchi et al. disclosed crystalline MWW type titanosilicate catalyst. A report by W. Fan, P. Wu, S, Namba, and T. Tatsumi (J. Catalyst 243 (2006) 183-191) disclosed a new titanosilicate molecular sieve with the structure analogous to MWW-type lamellar precursor. J. Ruan, P. Wu B. Slater and O. Terasaki disclosed detailed structure of Ti-YNU-1 (Angew. Chem. Int. Ed., 2005, 44, 6719) similar to ISE-MWW.

These closely related materials may further be distinguished by comparing XRD diffraction patterns for d-spacing maxima corresponding to (002), (100), (101) and (102) reflections for both as-synthesized and calcined materials. The d-spacing maximum corresponding to (002) reflection is typically in the range from 14.17 to 12.57 Angstroms (~6.15-7.05 deg 2-θ Cu Kα radiation). The d-spacing maximum corresponding to (100) reflection is typically in the range from 12.1 to 12.56 Angstroms (~7.3-7.05 deg 2-θ). The d-spacing maximum corresponding to (101) reflection is typically in the range from 10.14 to 12.0 Angstroms (8.7-7.35 deg 2-θ). The d-spacing maximum corresponding to (102) reflection is typically in the range from 8.66 to 10.13 Angstroms (10.2-8.7 deg 2-θ). The following table (Table 1) summarizes the differences between MCM-22, MCM-49, EMM-10, MCM-56 and the titanosilicate material reported by Tatsumi et al. based on the existence and/or the feature of XRD diffraction pattern for d-spacing maxima corresponding to (002), (100), (101) and (102) reflections for both as-synthesized and calcined materials.

TABLE 1

|  | As-synthesized | | | | Calcined | | | |
|---|---|---|---|---|---|---|---|---|
| XRD | (002) | (100) | (101) | (102) | (002) | (100) | (101) | (102) |
| MCM-22 | MCM-22-P | | | | MCM-22 | | | |
|  | Yes | Yes | Yes | Yes | No | Yes | Yes | Yes |
|  | All four peaks are resolved. A valley exists between (101) and (102), wherein the measured intensity corrected for background at the lowest point being less than 50% of the point at the same XRD d-spacing on the line connecting maxima for (101) and (102). | | | | Peak corresponding to (002) is not visible. All other three peaks are resolved. A valley exists between (101) and (102), wherein the measured intensity corrected for background at the lowest point being less than 50% of the point at the same XRD d-spacing on the line connecting maxima for (101) and (102). | | | |
| EMM-10 | EMM-10-P | | | | EMM-10 | | | |
|  | Yes | Yes | Non-discrete | | Yes | Yes | Non-discrete | |
|  | Both (002) peak and (100) peak are resolved, wherein the peak intensity for (002) is at least as great as 90% of the peak intensity of the d-spacing maximum for (100). Further, peaks corresponding to (101) and (102) are non-discrete or exhibit a valley but with measured intensity corrected for | | | | Peak corresponding to (002) is not visible. Peak corresponding to (100) is well resolved. And, peaks corresponding to (101) and (102) are non-discrete or exhibit a valley but with measured intensity corrected for background at the lowest point being not less than 50% | | | |

TABLE 1-continued

| XRD | As-synthesized | | | | Calcined | | | |
|---|---|---|---|---|---|---|---|---|
| | (002) | (100) | (101) | (102) | (002) | (100) | (101) | (102) |
| | background at the lowest point being not less than 50% of the point at the same XRD d-spacing on the line connecting maxima for (101) and (102). | | | | of the point at the same XRD d-spacing on the line connecting maxima for (101) and (102). | | | |
| MCM-22 family material as disclosed in U.S. Patent App. No. 11/827,953 | As-synthesized | | | | Calcined | | | |
| | Yes | Yes | Yes | Yes | No | Yes | Yes | Yes |
| | Peaks corresponding to (002) and (100) are well resolved. And, peaks corresponding to (101) and (102) are non-discrete peaks at a d-spacing maximum between 8.8 to 11 Angstroms, wherein the peak intensity of the (002) is less than 90% of the peak intensity of the (100). | | | | Peak corresponding to (002) is not visible. All other three peaks are resolved. A valley exists between (101) and (102), wherein the measured intensity corrected for background at the lowest point being less than 50% of the point at the same XRD d-spacing on the line connecting maxima for (101) and (102). | | | |
| MCM-49 | MCM-49-P | | | | MCM-49 | | | |
| | No | Yes | Yes | Yes | No | Yes | Yes | Yes |
| | Peak corresponding to (002) is not visible or as a shoulder peak. Peak corresponding to (100) is well resolved. And, peaks corresponding to (101) and (102) are resolved or exhibit a valley but with measured intensity corrected for background at the lowest point being not greater than 50% of the point at the same XRD d-spacing on the line connecting maxima for (101) and (102). | | | | Peak corresponding to (002) is not visible or as a shoulder peak. Peak corresponding to (100) is well resolved. And, peaks corresponding to (101) and (102) are resolved or exhibit a valley but with measured intensity corrected for background at the lowest point being not greater than 50% of the point at the same XRD d-spacing on the line connecting maxima for (101) and (102). | | | |
| MCM-56 | MCM-56-P | | | | MCM-56 | | | |
| | No | Yes | non-discrete | | No | Yes | non-discrete | |
| | Peak corresponding to (002) is not visible. Peak corresponding to (100) is well resolved. Peaks corresponding to (101) and (102) are non-discrete scattering. | | | | Peak corresponding to (002) is not visible. Peak corresponding to (100) is well resolved. Peaks corresponding to (101) and (102) are non-discrete or exhibit a valley but with measured intensity corrected for background at the lowest point being not less than 50% of the point at the same XRD d-spacing on the line connecting maxima for (101) and (102). | | | |
| MWW material | Precursor (US Patent Publication 20050158238, FIG. 4) | | | | Calcined (US Patent Publication 20050158238 FIG. 2) | | | |
| | Yes | Yes | Yes | Yes | No | Yes | Yes | Yes |
| | All four peaks are resolved. A valley exists between (101) and (102), wherein the measured intensity corrected for background at the lowest point being less than 50% of the point at the same XRD d-spacing on the line connecting maxima for (101) and (102). | | | | Only three peaks are resolved. A valley exists between (101) and (102), wherein the measured intensity corrected for background at the lowest point being less than 50% of the point at the same XRD d-spacing on the line connecting maxima for (101) and (102). | | | |
| Ti-MCM-22 | Precursor (J. Catal., Table 1) | | | | Calcined (US20050158238 FIG. 1) | | | |
| | Yes | Yes | Yes | Yes | Yes/No | Yes | Yes | Yes |
| | All four peaks reported for Si/Ti = 106. | | | | All four peaks are resolved for Si/Ti higher than 70. Only three peaks for Si/Ti less than 70. A valley exists between (101) and (102), wherein the measured intensity corrected for background at the lowest point being less than 50% of the point at the same XRD d-spacing on the line connecting maxima for (101) and (102). | | | |

It is known that crystal morphology, size and aggregation/agglomeration, or new x-ray diffraction can affect catalyst behavior, especially regarding catalyst activity and stability. There is, therefore, a need for novel crystalline molecular sieve compositions and method of making such novel crystalline molecular sieve compositions.

SUMMARY OF THIS DISCLOSURE

In some embodiments, this disclosure relates to an EMM-12 molecular sieve having, in its as-synthesized form and in calcined form, an X-ray diffraction pattern including peaks having a d-spacing maximum in the range of 14.17 to 12.57

Angstroms (~6.15-7.05 deg 2-θ Cu Kα), a d-spacing maximum in the range of 12.1 to 12.56 Angstroms (~7.3-7.05 deg 2-θ Cu Kα), and non-discrete scattering between about 8.66 to 12.0 Angstroms or exhibit a valley in between the peaks having a d-spacing maximum in the range of 10.14 to 12.0 Angstroms (8.7-7.35 deg 2-θ Cu Kα) and a d-spacing maximum in the range from 8.66 to 10.13 Angstroms (10.2-8.7 deg 2-θ) but with measured intensity corrected for background at the lowest point being not less than 50% of the point at the same XRD d-spacing on the line connecting maxima in the range of 10.14 to 12.0 Angstroms (8.7-7.35 deg 2-θ Cu Kα) and in the range from 8.66 to 10.13 Angstroms (10.2-8.7 deg 2-θ Cu Kα).

In other embodiments, this disclosure relates to an EMM-12 molecular sieve having, in its as-synthesized form and in calcined form, an X-ray diffraction pattern including peaks at d-spacing maxima at 13.5±0.25, 12.33±0.23, and non-discrete scattering between about 8.66 to 12.0 Angstroms or exhibit a valley in between the peaks at 11.05±0.3 and 9.31±0.3 Angstroms but with measured intensity corrected for background at the lowest point being not less than 50% of the point at the same XRD d-spacing on the line connecting maxima at around 11.05±0.18 and 9.31±0.13 Angstroms.

In other embodiments, this disclosure relates to a method of manufacturing an as-synthesized crystalline molecular sieve EMM-12, the method comprising the steps of:
(a) providing a mixture comprising EMM-10-P family composition, acidic composition, and optionally spacing agent;
(b) treating the mixture at treatment conditions to form a product comprising as-synthesized EMM-12; and
(c) recovering the as-synthesized crystalline EMM-12 molecular sieve.

In other embodiments, the as-synthesized crystalline molecular sieve EMM-12 is further calcined under calcination conditions to form calcined EMM-12, wherein the calcination conditions comprise a temperature in the range of 300 to 700° C. for a time in the range of 1 min to 500 hours.

In some aspects, the EMM-12 molecular sieve further comprises, in its as-synthesized form and in calcined form, an X-ray diffraction pattern including peaks at 3.57±0.07 and 3.42±0.07 Angstroms.

In other aspects, the EMM-12 molecular sieve further comprises, in its as-synthesized form and in calcined form, an X-ray diffraction pattern including peak at 6.9±0.15 Angstroms.

In yet other aspects, the EMM-12 molecular sieve has a composition involving the molar relationship:

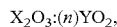

$X_2O_3:(n)YO_2$, wherein X is a trivalent element comprises at least one of aluminum, boron, iron and gallium, Y is a tetravalent element comprises at least one of silicon and germanium, and n is at least about 10. In the as-synthesized form the EMM-12 molecular sieve has a formula, on an anhydrous basis and in terms of moles of oxides per n moles of $YO_2$, as follows:

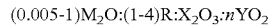

$(0.005-1)M_2O:(1-4)R:X_2O_3:nYO_2$ wherein M is an alkali or alkaline earth metal, and R is an organic moiety. In a preferred embodiment, n is from about 10 to about 150, more preferably from about 10 to about 50. In some preferred embodiment, X is aluminum and Y is silicon.

In some embodiments, the EMM-12 calcined molecular sieve has a collidine adsorption capacity of at least 150 mmoles/g, preferably at least 250 mmoles/g.

These and other facets of the present invention shall become apparent from the following detailed description, Figures, and appended claims.

DETAILED DESCRIPTION

Introduction

Figure 1:
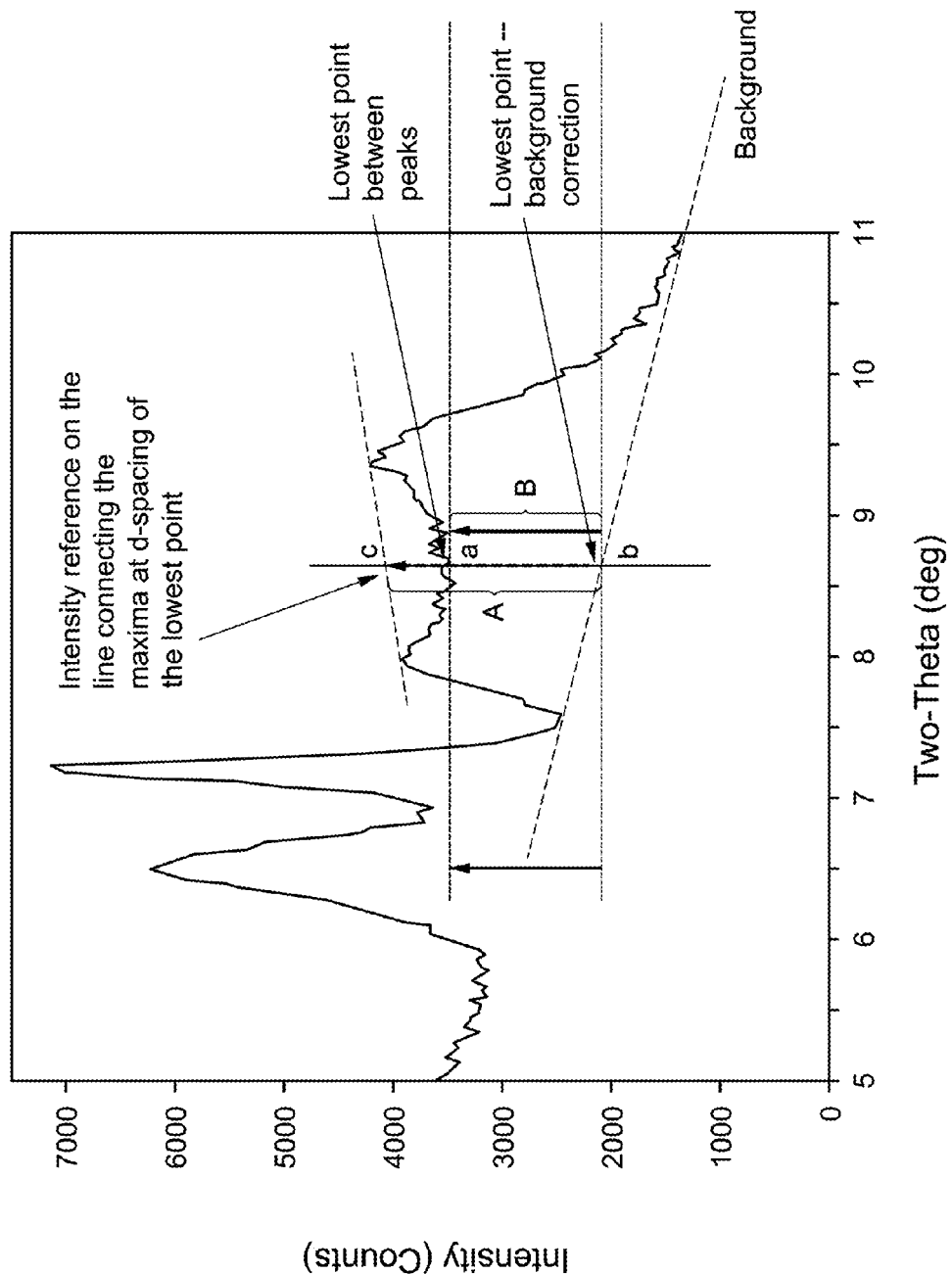
FIG. 1 shows the XRD pattern between 5 to 11 degree 2-θ of Example 1.

All patents, patent applications, test procedures (such as ASTM methods, UL methods, and the like), priority documents, articles, publications, manuals, and other documents cited herein are fully incorporated by reference to the extent such disclosure is not inconsistent with the present invention and for all jurisdictions in which such incorporation is permitted.

When numerical lower limits and numerical upper limits are listed herein, ranges from any lower limit to any upper limit are contemplated. While the illustrative embodiments of the disclosure have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside in the present disclosure, including all features which would be treated as equivalents thereof by those skilled in the art to which the disclosure pertains.

As used in this specification, the term "framework type" is used in the sense described in the "Atlas of Zeolite Framework Types," 2001.

As used herein, the numbering scheme for the Periodic Table Groups is used as in Chemical and Engineering News, 63(5), 27 (1985).

X-Ray Powder Diffraction Pattern

The interplanar spacings, d's, were calculated in Angstrom units (Å), and the relative intensities of the lines, $I/I_o$, where the intensity of the strongest line above background, $I_o$, is counted as 100, were derived with the use of a profile fitting routine (or second derivative algorithm). The intensities are uncorrected for Lorentz and polarization effects. The relative intensities are given in terms of the symbols VS=very strong (greater than 60 to 100), S=strong (greater than 40 to 60), M=medium (greater than 20 to 40) and W=weak (0 to 20). It should be understood that diffraction data listed as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, and thermal and/or hydrothermal history. Other changes in diffraction patterns can be indicative of important differences between materials, which is the case for comparing MCM-22 with similar materials, e.g., MCM-49, MCM-56, and PSH-3.

The interplanar spacings, d's, were considered broad if they exhibited peak width of about 1.5° or more at half height determined as 50% intensity value from the maximum to the baseline.

The term "XRD distinguishable peak" as used herein is defined as XRD peak with clearly defined peak maximum, which is at least two times of the average background noise level.

The term "non-discrete" peaks (also "unresolved" peaks) in XRD as used herein means peaks having a monotonic profile in-between them (successive points either consistently increasing (or staying even) or decreasing (or staying even) within noise).

The term "discrete" peaks (also "resolved" peaks) in XRD as used herein means XRD peak(s) which are not non-discrete (unresolved).

FIG. 1 graphically demonstrates the XRD pattern between 5 to 11 degree 2-θ of the product of Example 1. The measured intensity corrected for background at the lowest point between d-spacing maxima in the range of 10.14 to 12.0 Angstroms and in the range from 8.66 to 10.13 Angstroms, represented as B, is the distance between the lowest point (point a) and the point (point b) on the line of the background correction line at the same XRD d-spacing of the lowest point (point a). The distance between the point b and the point (point c) on the line connecting d-spacing maxima in the range of 10.14 to 12.0 Angstroms and in the range from 8.66 to 10.13 Angstroms at the same XRD d-spacing of the lowest point is represented as A.

Composition Matter of EMM-12

In some embodiments, the composition matter of EMM-12 has, in as-synthesized form and in calcined form, an X-ray diffraction pattern including peaks having a d-spacing maximum in the range of 14.17 to 12.57 Angstroms (~6.15-7.05 deg 2-θ Cu Kα), such as, at 13.5±0.25, a d-spacing maximum in the range of 12.1 to 12.56 Angstroms (~7.3-7.05 deg 2-θ), such as, 12.33±0.23, and non-discrete scattering between about 8.66 to 12.0 Angstroms or exhibit a valley in between the peaks having a d-spacing maximum in the range of 10.14 to 12.0 Angstroms (8.7-7.35 deg 2-θ), such as, at 11.05±0.3, and a d-spacing maximum in the range from 8.66 to 10.13 Angstroms (10.2-8.7 deg 2-θ), such as, at 9.31±0.3 Angstroms, with measured intensity corrected for background at the lowest point being not less than 50% of the point at the same XRD d-spacing on the line connecting d-spacing maximum in the range of 10.14 to 12.0 Angstroms (8.7-7.35 deg 2-θ) and d-spacing maximum in the range from 8.66 to 10.13 Angstroms (10.2-8.7 deg 2-θ).

In some embodiments, the composition matter of EMM-12 has, in as-synthesized form and in calcined form, an X-ray diffraction pattern including peaks at d-spacing maxima at 13.5±0.25, 12.33±0.23, and non-discrete scattering between about 8.85 to 11.05 Angstroms or exhibit a valley in between the peaks at 11.05±0.3 and 9.31±0.3 Angstroms but with measured intensity corrected for background at the lowest point being not less than 50% of the point at the same XRD d-spacing on the line connecting maxima at around 11.05±0.18 and 9.31±0.13 Angstroms.

In further embodiments, the composition matter of EMM-12 further has, in as-synthesized form and in calcined form, an X-ray diffraction pattern including peaks at d-spacing maxima at 3.57±0.06 and 3.43±0.06 Angstroms. In yet further embodiments, the composition matter of EMM-12 further has, in as-synthesized form and in calcined form, an X-ray diffraction pattern including peak at d-spacing maximum at 6.9±0.15 Angstroms. In yet further embodiments, the composition matter of EMM-12 further has, in as-synthesized form and in calcined form, an X-ray diffraction pattern including peak at d-spacing maximum at 3.96±0.08 Angstroms.

In other embodiments, the composition matter of EMM-12 has, in as-synthesized form and in calcined form, an X-ray diffraction pattern including peaks at d-spacing maxima and relative intensities at 13.5±0.25 (M-VS), 12.33±0.23 (M-VS), and non-discrete scattering between about 8.85 to 11.05 Angstroms (W-S) or exhibit a valley in between the peaks at 11.05±0.18 (W-S) and 9.31±0.13 (W-S) Angstroms but with measured intensity corrected for background at the lowest point being not less than 50% of the point at the same XRD d-spacing on the line connecting maxima at around 11.05±0.18 and 9.31±0.13 Angstroms.

TABLE 2

| Interplanar d-Spacing (Å) | Relative Intensity, I/I$_o$ × 100 |
|---|---|
| 14.17 > d > 12.57 | M-VS |
| 12.56 > d > 12.1 | M-VS |
| 12.0 > d > 10.14 | W_S |
| 10.13 > d > 8.66 | W-S |
| 6.9 ± 0.15 | W-M, broad |
| 3.96 ± 0.08 | W-VS, broad |
| 3.57 ± 0.06 | W-M |
| 3.43 ± 0.06 | M-VS |

In other embodiments, the composition matter of EMM-12 further has, in as-synthesized form and in calcined form, an X-ray diffraction pattern including peaks at d-spacing maxima at 3.57±0.06 (W-M) and 3.43±0.06 (M-VS) Angstroms. In yet further embodiments, the composition matter of EMM-12 further has, in as-synthesized form and in calcined form, an X-ray diffraction pattern including peak at d-spacing maximum at 6.9±0.15 Angstroms (W-M, broad). In yet further embodiments, the composition matter of EMM-12 further has, in as-synthesized form and in calcined form, an X-ray diffraction pattern including peak at d-spacing maximum at 3.96±0.08 Angstroms (W-VS, broad).

In some preferred embodiments, the X-ray diffraction pattern of the crystalline molecular sieve EMM-12 further has peaks at d-spacing maxima and intensities listed in Table 2.

In some embodiments, the X-ray diffraction pattern of the crystalline molecular sieve EMM-12 of this disclosure further includes a d-spacing maximum at 28±2 Angstroms.

In some embodiments, the EMM-12 exhibits an extraordinary high collidine number of greater than 150 µmoles/g, preferably greater than 200 µmoles/g, more preferably greater than 250 µmoles/g, even more preferably greater than 300 µmoles/g, and most preferably greater than 350 µmoles/g, compared for up to about 200 µmoles/g for EMM-10 and 120 mmoles/g for MCM-22.

Chemical Composition of as-Synthesized EMM-12 and Calcined EMM-12

The as-synthesized EMM-12 molecular sieve material of this disclosure may have a composition, in terms of mole ratios of oxides:

$YO_2/X_2O_3$ in the range of 10 to infinity or in the range of 10 to 50;

$M/X_2O_3$ in the range of 0.005-0.1; and $R/X_2O_3$ in the range of 1-4.

The calcined EMM-12 molecular sieve material of this disclosure may be prepared by calcining as-synthesized EMM-12 under calcination conditions to remove at least the majority of the organic template R from the as-synthesized EMM-12.

Process of Making EMM-12

In some embodiments, this disclosure relates to a method of manufacturing an as-synthesized crystalline molecular sieve EMM-12, the method comprising the steps of:
(a) providing a mixture comprising EMM-10-P family composition and acidic composition, optionally a spacing agent;
(b) treating the mixture at treatment conditions to form a product comprising as-synthesized EMM-12; and
(c) recovering the acid treated crystalline molecular sieve.

In some preferred embodiments, the as-synthesized EMM-12 is made by a process comprising:
(1) providing a mixture comprising EMM-10-P having $Si/Al_2$ in the range from 10-infinity, preferable from about 10 to 150, and acidic composition comprising at least one of nitric acid, sulfuric acid, hydrochloric acid; oxalic acid, wherein said acid has a concentration of less than or equal to 10 N, preferably less than 1N, optionally a spacing agent comprising at least one of dimethyldiethoxy silane, diethyldiethoxy silane, and tetraethyl silane (TEOS), preferable TEOS; and
(2) treating the mixture of step (1) to treatment conditions, wherein the treatment conditions comprise a temperature in the range of 50-170° C. for a time in the range of 1-24 hrs, optionally with a stirring speed in the range of 0-1000 RPM.

The mixture of step (a) comprises EMM-10-P family composition, acidic composition, and optionally a spacing agent, wherein the weight ratio of the solid content of the EMM-10-P family composition over the acidic composition and the weight ratio of the spacing agent over the solid content of the EMM-10-P family composition are listed in the following table (Table 3). Useful and preferred ranges of the treatment temperature and treatment time are also listed in Table 3.

TABLE 3

|  | Useful range | Preferred range | Most preferred range |
|---|---|---|---|
| Solid content (wt) Acidic composition | 0.001-1000 | 0.01-100 | 0.1-10 |
| Spacing agent (wt) Solid content (wt) | 0-2 | 0-1 | 0.01-0.5 |
| Acid concentration (N) | 0.001-10 | 0.001-5 | 0.01-2 |
| Temperature (° C.) | 25-250 | 50-200 | 90-170 |
| Time (hr) | 0.01-240 | 1-48 | 1-24 |

The following solid content over acidic composition weight ratios are useful lower limits: 0.001, 0.01, 0.05, 0.1, 0.5, 1, 5, 10, 50, 100 and 500. The following solid content over acidic composition weight ratios are useful upper limits: 0.01, 0.05, 0.1, 0.5, 1, 5, 10, 50, 100, 500 and 1000. The solid content over acidic composition weight ratio falls in a range between any one of the above-mentioned lower limits and any one of the above-mentioned upper limits, so long as the lower limit is less than or equal to the upper limit. The solid content over acidic composition weight ratio may be present in an amount ranging from 0.01 to 100 in one embodiment, alternatively 0.1 to 10, alternatively 0.1 to 5.

The following ratios are useful lower spacing agent over solid content weight ratio limits: 0, 0.001, 0.01, 0.05, 0.1, 0.5, 1, and 1.5. The following ratios are useful upper spacing agent over solid content weight ratio limits: 0.001, 0.01, 0.05, 0.1, 0.5, 1, 1.5, and 2. The spacing agent over solid content weight ratio falls in a range between any one of the above-mentioned lower spacing agent over solid content weight ratio limits and any one of the above-mentioned upper spacing agent over solid content weight ratio limits, so long as the lower spacing agent over solid content weight ratio limit is less than or equal to the upper spacing agent over solid content weight ratio limit. The spacing over solid content weight ratio may be present in an amount ranging from 0 to 2 in one embodiment, alternatively 0 to 1, and alternatively 0.1 to 0.5.

The following temperatures (° C.) are useful lower treatment temperature limits: 25, 50, 60, 70, 80, 90, 100, 110, 120, 130, 140, 150, 160, 170, and 200. The following temperatures (° C.) are useful upper treatment temperature limits: 50, 60, 70, 80, 90, 100, 110, 120, 130, 140, 150, 160, 170, 180, 190, 200, 210, 220, 230, 240, and 250. The treatment temperature (° C.) falls in a range between any one of the above-mentioned lower treatment temperature limits and any one of the above-mentioned upper treatment temperature limits, so long as the lower treatment temperature limit is less than or equal to the upper treatment temperature limit. The treatment temperature may be present in an amount ranging from 25° C. to 250° C. in one embodiment, alternatively 70° C. to 200° C., and alternatively 90° C. to 170° C.

The following times (hr) are useful lower time limits for treatment: 0.01, 1, 5, 10, 20, 30, 50, 100, and 150. The following time (hr) are useful upper time limits for treatment: 1, 5, 10, 20, 40, 50, 70, 100, 150, 200, and 240. The time (hr) for treatment falls in a range between any one of the above-mentioned lower time limits for treatment and any one of the above-mentioned upper time limits for treatment, so long as the lower time limit for treatment is less than or equal to the upper time limit for treatment. The time for treatment may be present in an amount ranging from 1 to 100 in one embodiment, alternatively 1 to 48, and alternatively 1 to 24.

(1) EMM-10-P Family Composition

EMM-10-P family composition as used herein comprises at least one of EMM-10-P composition disclosed in U.S. patent application Ser. No. 11/823,129 (its entirety of which is enclosed herein by reference) and as-synthesized MCM-22 family molecular sieve composition disclosed in U.S. patent application Ser. No. 11/827,953 (its entirety of which is enclosed herein by reference).

The EMM-10-P composition relates to a crystalline molecular sieve, designated as EMM-10-P, having, in its as-synthesized form, an X-ray diffraction pattern including d-spacing maxima at 13.18±0.25 and 12.33±0.23 Angstroms, wherein the peak intensity of the d-spacing maximum at 13.18±0.25 Angstroms is at least as great as 90% of the peak intensity of the d-spacing maximum at 12.33±0.23 Angstroms. In addition, the X-ray diffraction pattern of the EMM-10-P molecular sieve further includes two XRD distinguishable peaks with d-spacing maxima at 11.06±0.18 and 9.25±0.13 Angstroms, wherein the peak intensity of the d-spacing maximum at 11.06±0.18 Angstroms is at least as great as the peak intensity of the d-spacing maximum at 9.25±0.13 Angstroms. Additionally, the peaks with d-spacing maxima at 11.06±0.18 and 9.25±0.13 Angstroms may be non-discrete peaks.

Further the EMM-10-P relates to a crystalline MCM-22 family molecular sieve that has a total surface area of greater than 450 m²/g as measured by the N₂ BET method, and preferably has a ratio of the external surface area over the total surface area of less than 0.15 after conversion into H-form by exchange with ammonium nitrate and calcination, wherein the external surface area is determined from a t-plot of the N₂ BET.

Additionally, the EMM-10-P relates to a MCM-22 family crystalline molecular sieve that has a morphology of tabular habit, wherein at least 50 wt % of the crystalline molecular sieve have a crystal diameter greater than 1 μm as measured by the SEM, preferably greater than 2 μm as measured by the SEM, preferably at least 50 wt % of the crystalline molecular sieve have a crystal thickness of about 0.025 μm as measured by the SEM.

U.S. patent application Ser. No. 11/827,953, its entirety of which is enclosed herein by reference, discloses a novel crystalline MCM-22 family molecular sieve having, in its as-synthesized form, an X-ray diffraction pattern including a peak at d-spacing maximum of 12.33±0.23 Angstroms, a distinguishable peak at a d-spacing maximum between 12.57 to about 14.17 Angstroms and a non-discrete peak at a d-spacing maximum between 8.8 to 11 Angstroms, wherein the peak intensity of the d-spacing maximum between 12.57 to about 14.17 Angstroms is less than 90% of the peak intensity of the d-spacing maximum at 12.33±0.23 Angstroms.

The EMM-10-P as disclosed in U.S. patent application Ser. No. 11/827,953, may be made by crystallizing a mixture having a composition in molar ratio listed in Table 4.

TABLE 4

| Reactants | Useful | Preferred |
|---|---|---|
| YO₂/X₂O₃ | 10 to infinity | 15-55 |
| H₂O/YO₂ | 1 to 10000 | 5-35 |
| OH⁻/YO₂* | 0.001-0.39 | 0.1-0.35 |
| OH⁻/YO₂** | 0.001-0.59 | 0.1-0.5 |
| M/YO₂ | 0.001-2 | 0.1-1 |
| R/YO₂ | 0.001-2 | 0.01-0.5 |
| Seed*** | 0-25 wt % | 1-5 wt % |
| R | Me₆-diquat-5 salt(s) | Me₆-diquat-5 salt(s) |

After crystallization, the EMM-10-P product has a composition in molar ratio listed in Table 5.

TABLE 5

| Reactants | Useful | Preferred |
|---|---|---|
| YO₂/X₂O₃ | 10 to infinity | |
| M/X₂O₃ | 0.005-0.1 | |
| R/X₂O₃ | 1-4 | |
| R | Me₆-diquat-5 salt(s) | Me₆-diquat-5 salt(s) |

U.S. patent application Ser. No. 11/827,953, its entirety of which is enclosed herein by reference, discloses a novel crystalline MCM-22 family molecular sieve. The as-synthesized composition disclosed in U.S. patent application Ser. No. 11/827,953 is a novel crystalline MCM-22 family molecular sieve having, in its as-synthesized form, an X-ray diffraction pattern including a peak at a d-spacing maximum of 12.33±0.23 Angstroms, a distinguishable peak at a d-spacing maximum between 12.57 to about 14.17 Angstroms and a non-discrete peak at a d-spacing maximum between 8.8 to 11 Angstroms, wherein the peak intensity of the d-spacing maximum between 12.57 to about 14.17 Angstroms is less than 90% of the peak intensity of the d-spacing maximum at 12.33±0.23 Angstroms. The as-synthesized composition of U.S. patent application Ser. No. 11/827,953 may further comprises XRD peaks at d-spacing maxima at 3.57±0.06 and 3.43±0.06 Angstroms and/or a d-spacing maximum at 28±1 Angstroms.

Furthermore, the X-ray diffraction pattern of the as-synthesized composition of U.S. patent application Ser. No. 11/827,953 includes values and relative intensities substantially as shown in Table 6:

TABLE 6

| Interplanar d-Spacing (Å) | Relative Intensity, I/I₀ × 100 |
|---|---|
| 14.17 > d > 12.57 | M-VS |
| 12.33 ± 0.23 | M-VS |
| 11.1 to 8.8 | W-S |
| 4.41 ± 0.1 | W-M, broad |
| 3.96 ± 0.08 | W-VS, broad |
| 3.57 ± 0.06 | W-M |
| 3.43 ± 0.06 | M-VS |

The solid content of an EMM-10-P family composition used in the weight ratio of the solid content of the EMM-10-P family composition over the acidic composition and the weight ratio of the spacing agent over the solid content of the EMM-10-P family composition is calculated by the total weight of tetravalent element oxide and trivalent element oxide in an EMM-10-P family composition.

(2) Acidic Compositions

The acidic composition useful for this disclosure comprises an acidic solute and a solvent. The acidic solute comprises at least one of inorganic acid, such as, nitric acid hydrochloric acid and sulfuric acid, and organic acid, such as, oxalic acid and acetic acid, or any combination of inorganic acid and organic acid. Preferably, the acidic solute is nitric acid. The solvent comprises at least one of water, methanol, ethanol, acetone and dimethylsulfone (DMSO).

The acid concentration of the acidic composition is in the range of 0.001 to 10. The following acid concentrations are useful lower limits: 0.001, 0.01, 0.05, 0.1, 0.5, 1, 2, 3, 4, 5, 6, 7, 8, and 9. The following acid concentrations are useful upper limits: 0.01, 0.05, 0.1, 0.5, 1, 2, 3, 4, 5, 6, 7, 8, 9, and 10. The acid concentration falls in a range between any one of the above-mentioned lower limits and any one of the above-mentioned upper limits, so long as the lower limit is less than or equal to the upper limit. The acid concentration may be present in an amount ranging from 0.001 to 5 in one embodiment, alternatively 0.01 to 4, and alternatively 0.1 to 2.

The weight of acidic composition as used in the solid content over acidic composition weight ratios is calculated based on the total weight of acidic solute and solvent.

(3) Optional Spacing Agent

Optionally, the acidic treatment step also comprises a spacing agent. The spacing agent useful is any agent capable of providing a silicon moiety that can stabilize the precursor in expanded form (i.e. having the distinct (002) peak at 13.5±0.25 in both as-synthesized and calcined forms).

Examples of compounds for spacing include organo-compounds of a tetravalent element, a trivalent element, and/or pentavalent compounds, such as, organosilicon compound, organogermanium compound, organotitanium compounds, organoboron compounds, organoaluminum compound, and organophorphous compound. The organosilicon silicon compounds may comprise a polysiloxane include silicones, a siloxane, and a silane including disilanes and alkoxysilanes.

Silicone compounds that can be used in the present invention include the following:

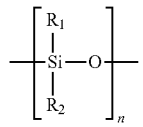

wherein $R_1$ is hydrogen, fluoride, hydroxy, alkyl, aralkyl, alkaryl or fluoro-alkyl. The hydrocarbon substituents generally contain from 1 to about 10 carbon atoms and preferably are methyl or ethyl groups. $R_2$ is selected from the same group as $R_1$, and n is an integer of at least 2 and generally in the range of 2 to about 1000. The molecular weight of the silicone compound employed is generally between about 80 to about 20,000 and preferably about 150 to about 10,000. Representative silicone compounds include dimethylsilicone, diethylsilicone, phenylmethylsilicone, methyl hydrogensilicone, ethylhydrogensilicone, phenylhydrogensilicone, fluoropropylsilicone, ethyltrifluoroprophysilicone, tetrachlorophenyl methyl methylethylsilicone, phenylethylsilicone, diphenylsilicone, methyltrisilicone, tetrachlorophenylethyl silicone, methylvinylsilicone and ethylvinylsilicone. The silicone compound need not be linear but may be cyclic as for example hexamethylcyclotrisiloxane, octamethylcyclotetrasiloxane, hexaphenyl cyclotrisiloxane and octaphenylcyclotetrasiloxane. Mixtures of these compounds may also be used as well as silicones with other functional groups.

Useful siloxanes and polysiloxanes include as non-limiting example hexamethylcyclotrisiloxane, octamethylcyclotetrasiloxane, decamethyl cyclopentasiloxane, hexamethyldisiloxane, octamethylrisiloxane, decamethyltetrasiloxane, hexaethylcyclotrisiloxane, octaethylcyclo tetrasiloxane, hexaphenylcyclotrisiloxane and octaphenylcyclo-tetrasiloxane.

Useful silanes, disilanes, or alkoxysilanes include organic substituted silanes having the general formula:

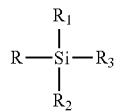

wherein R is a reactive group such as hydrogen, alkoxy, halogen, carboxy, amino, acetamide, trialkylsilyoxy, $R_1$, $R_2$ and $R_3$ can be the same as R or can be an organic radical which may include alkyl of from 1 to about 40 carbon atoms, alkyl or aryl carboxylic acid wherein the organic portion of alkyl contains 1 to about 30 carbon atoms and the aryl group contains about 6 to about 24 carbons which may be further substituted, alkylaryl and arylalkyl groups containing about 7 to about 30 carbon atoms. Preferably, the alkyl group for an alkyl silane is between about 1 and about 4 carbon atoms in chain length. Mixtures may also be used.

The silanes or disilanes include, as non-limiting examples, dimethylphenylsilane, phenylrimethylsilane, triethylsilane and hexamethyldislane. Useful alkoxysilanes are those with at least one silicon-hydrogen bond.

Catalysis and Adsorption

A summary of the molecular sieves and/or zeolites, in terms of production, modification and characterization of molecular sieves, is described in the book "Molecular Sieves—Principles of Synthesis and Identification"; (R. Szostak, Blackie Academic & Professional, London, 1998, Second Edition). In addition to molecular sieves, amorphous materials, chiefly silica, aluminum silicate and aluminum oxide, have been used as adsorbents and catalyst supports. A number of long-known forming techniques, like spray drying, pilling, pelletizing and extrusion, have been and are being used to produce macrostructures in the form of, for example, spherical particles, extrudates, pellets and Tablets of both micropores and other types of porous materials for use in catalysis, adsorption and ion exchange. A summary of these techniques is described in "Catalyst Manufacture," A. B. Stiles and T. A. Koch, Marcel Dekker, New York, 1995.

To the extent desired, the original metal cations of the as-synthesized material can be replaced in accordance with techniques well known in the art, at least in part, by ion exchange with other cations. Preferred replacing cations include metal ions, hydrogen ions, hydrogen precursor, e.g., ammonium, ions and mixtures thereof. Particularly preferred cations are those which tailor the catalytic activity for certain hydrocarbon conversion reactions. These include hydrogen, rare earth metals and metals of Groups 1-17, preferably Groups 2-12 of the Periodic Table of the Elements.

The EMM-12 crystalline molecular sieve of this disclosure when employed either as an adsorbent or as a catalyst in an organic compound conversion process should be generally dehydrated, at least partially. This can be done by heating to a temperature in the range of e.g., 200° C. to 595° C. in an atmosphere such as air or nitrogen, and at atmospheric, sub-atmospheric or super-atmospheric pressures for e.g., between 30 minutes and 48 hours. The degree of dehydration is measured by the percentage of weight loss relative to the total weight loss of a molecular sieve sample at 595° C. under flowing dry nitrogen (less than 0.001 kPa partial pressure of water vapor) for 48 hours. Dehydration can also be performed at room temperature (~25° C.) merely by placing the silicate in a vacuum, but a longer time is required to obtain a sufficient amount of dehydration.

The EMM-12 crystalline molecular sieve of this disclosure especially in its metal, hydrogen and ammonium forms can be beneficially converted to another form by thermal treatment. This thermal treatment is generally performed by heating one of these forms at a temperature of at least 370° C. for at least 1 minute and generally not longer than 1000 hours. While sub-atmospheric pressure can be employed for the thermal treatment, atmospheric pressure is desired for reasons of convenience. The thermal treatment can be performed at a temperature up to about 925° C. The thermal treated product is particularly useful in the catalysis of certain hydrocarbon conversion reactions. The thermally treated product, especially in its metal, hydrogen and ammonium forms, is particularly useful in the catalysis of certain organic, e.g., hydrocarbon, conversion reactions. Non-limiting examples of such reactions include those described in U.S. Pat. Nos. 4,954,325; 4,973,784; 4,992,611; 4,956,514; 4,962,250; 4,982,033; 4,962,257; 4,962,256; 4,992,606; 4,954,663; 4,992,615; 4,983,276; 4,982,040; 4,962,239; 4,968,402; 5,000,839; 5,001,296; 4,986,894; 5,001,295; 5,001,283; 5,012,033; 5,019,670; 5,019,665; 5,019,664; and 5,013,422, each incorporated herein by reference as to the description of the catalytic reactions.

The EMM-12 crystalline molecular sieve of this disclosure can be shaped into a wide variety of particle sizes. Generally speaking, the particles can be in the form of a powder, a granule, or a molded product, such as an extrudate. In cases where the catalyst is molded, such as by extrusion, the crystals can be extruded before drying or partially dried and then extruded.

The EMM-12 crystalline molecular sieve of this disclosure may be used as an adsorbent, such as for separating at least one component from a mixture of components in the vapor or liquid phase having differential sorption characteristics with respect to the EMM-12 crystalline molecular sieve(s) of this disclosure. Therefore, at least one component can be partially or substantially totally separated from a mixture of components having differential sorption characteristics with respect to the EMM-12 crystalline molecular sieve(s) of this disclosure by contacting the mixture with the EMM-12 crystalline molecular sieve(s) of this disclosure to selectively sorb the one component.

The EMM-12 crystalline molecular sieve of this disclosure is useful as catalyst in a wide range of processes, including separation processes and hydrocarbon conversion processes. Specific examples of hydrocarbon conversion processes which are effectively catalyzed by the EMM-12 crystalline molecular sieve(s) of this disclosure by itself or in combination with one or more other catalytically active substances including other crystalline catalysts, include the following:

(i) alkylation of aromatic hydrocarbons, e.g., benzene, with long chain olefins, e.g., $C_{14}$ olefin, with reaction conditions including, individually or in any combination, a temperature of from about 340° C. to about 500° C., a pressure of from about 101 to about 20200 kPa-a (absolute), a weight hourly space velocity of from about 2 $hr^{-1}$ to about 2000 $hr^{-1}$ and an aromatic hydrocarbon/olefin mole ratio of from about 1/1 to about 20/1, to provide long chain alkyl aromatics which can be subsequently sulfonated to provide synthetic detergents;

(ii) alkylation of aromatic hydrocarbons with gaseous olefins to provide short chain alkyl aromatic compounds, e.g., the alkylation of benzene with propylene to provide cumene, with reaction conditions including, individually or in any combination, a temperature of from about 10° C. to about 125° C., a pressure of from about 101 to about 3030 kPa-a, and an aromatic hydrocarbon weight hourly space velocity (WHSV) of from 5 $hr^{-1}$ to about 50 $hr^{-1}$;

(iii) alkylation of reformate containing substantial quantities of benzene and toluene with fuel gas containing $C_5$ olefins to provide, inter alia, mono- and di-alkylates with reaction conditions including, individually or in any combination, a temperature of from about 315° C. to about 455° C., a pressure of from about 3000 to about 6000 kPa-a, a WHSV-olefin of from about 0.4 $hr^{-1}$ to about 0.8 $hr^{-1}$, a WHSV-reformate of from about 1 $hr^{-1}$ to about 2 $hr^{-1}$ and a gas recycle of from about 1.5 to 2.5 vol/vol fuel gas feed;

(iv) alkylation of aromatic hydrocarbons, e.g., benzene, toluene, xylene and naphthalene, with long chain olefins, e.g., $C_{14}$ olefin, to provide alkylated aromatic lube base stocks with reaction conditions including, individually or in any combination, a temperature of from about 160° C. to about 260° C. and a pressure of from about 2600 to 3500 kPa-a;

(v) alkylation of phenols with olefins or equivalent alcohols to provide long chain alkyl phenols with reaction conditions including, individually or in any combination, a temperature of from about 200° C. to about 250° C., a pressure of from about 1500 to 2300 kPa-a and a total WHSV of from about 2 $hr^{-1}$ to about 10 $hr^{-1}$;

(vi) conversion of light paraffins to olefins and aromatics with reaction conditions including, individually or in any combination, a temperature of from about 425° C. to about 760° C. and a pressure of from about 170 to about 15000 kPa-a;

(vii) conversion of light olefins to gasoline, distillate and lube range hydrocarbons with reaction conditions including, individually or in any combination, a temperature of from about 175° C. to about 375° C. and a pressure of from about 800 to about 15000 kPa-a;

(viii) two-stage hydrocracking for upgrading hydrocarbon streams having initial boiling points above about 260° C. to premium distillate and gasoline boiling range products in a first stage using the MCM-22 family molecular sieve of this disclosure in combination with a Groups 8-10 metal as catalyst with effluent therefrom being reaction in a second stage using zeolite Beta, also in combination with a Groups 8-10 metal, as catalyst, the reaction conditions including, individually or in any combination, a temperature of from about 340° C. to about 455° C., a pressure of from about 3000 to about 18000 kPa-a, a hydrogen circulation of from about 176 to about 1760 liter/liter and a liquid hourly space velocity (LHSV) of from about 0.1 to 10 $h^{-1}$;

(ix) a combination hydrocracking/dewaxing process in the presence of the MCM-22 family molecular sieve of this disclosure and a hydrogenation component as catalyst, or a mixture of such catalyst and zeolite Beta, with reaction conditions including, individually or in any combination, a temperature of from about 350° C. to about 400° C., a pressure of from about 10000 to about 11000 kPa-a, an LHSV of from about 0.4 to about 0.6 and a hydrogen circulation of from about 528 to about 880 liter/liter;

(x) reaction of alcohols with olefins to provide mixed ethers, e.g., the reaction of methanol with isobutene and/or isopentene to provide methyl-t-butyl ether (MTBE) and/or t-amyl methyl ether (TAM) with conversion conditions including, individually or in any combination, a temperature of from about 20° C. to about 200° C., a pressure of from 200 to about 20000 kPa-a, a WHSV (gram-olefin per hour gram-zeolite) of from about 0.1 $hr^{-1}$ to about 200 $hr^{-1}$ and an alcohol to olefin molar feed ratio of from about 0.1/1 to about 5/1;

(xi) toluene disproportionation with $C_9$+ aromatics as co-feed with reaction conditions including, individually or in any combination, a temperature of from about 315° C. to about 595° C., a pressure of from about 101 to about 7200 kPa-a, a hydrogen/hydrocarbon mole ratio of from about 0 (no added hydrogen) to about 10 and a WHSV of from about 0.1 $hr^{-1}$ to about 30 $hr^{-1}$;

(xii) preparation of the pharmaceutically-active compound 2-(4-isobutylphenyl) propionic acid, i.e. ibuprofen, by reacting isobutyl benzene with propylene oxide to provide the intermediate 2-(4-isobutylphenyl) propanol followed by oxidation of the alcohol to the corresponding carboxylic acid;

(xiii) use as an acid-binding agent in the reaction of amines with heterocyclic fiber-reactive components in preparation of dyes to prepare practically salt-free reactive dye-containing solution, as in German Patent No. DE 3,625,693, incorporated entirely herein by reference;

(xiv) as the absorbent for separating 2,6-toluene diisocyanate (2,6-TDI) from isomers if TDI as in U.S. Pat. No. 4,721,807, incorporated entirely herein by reference, whereby a feed mixture comprising 2,6-TDI and 2,4-TDI is contacted with the present MCM-22 family molecular sieve which has been cation-exchanged with K ions to absorb the 2,6-TDI, followed by recovering the 2,6-TDI by desorption with desorbent material comprising toluene;

(xv) as the absorbent for separating 2,4-TDI from its isomers as in U.S. Pat. No. 4,721,806, incorporated entirely herein by reference, whereby a feed mixture comprising 2,4-TDI and 2,6-TDI is contact with the present MCM-22 family molecular sieve which has been cation-exchanged with Na, Ca Li and/or Mg ions to absorb the 2,4-TDI, followed by recovering the 2,4-TDI by desorption with desorbent material comprising toluene;

(xvi) in a process for decreasing the durene content of a 90-200° C.+ bottoms fraction obtained from the catalytic conversion of methanol to gasoline which comprises contacting the durene-containing bottoms fraction with hydrogen over a catalyst of the present MCM-22 family molecular sieve with a hydrogenation metal, at conditions including, individually or in any combination, a temperature of from about 230° C. to about 425° C. and a pressure of from about 457 to about 22000 kPa-a;

(xvii) in a processes for co-producing phenol and ketones that proceed through benzene alkylation, followed by formation of the alkylbenzene hydroperoxide and cleavage of the alkylbenzene hydroperoxide into phenol and ketone, e.g., benzene and propylene to phenol and acetone, benzene and $C_4$ olefins to phenol and methyl ethyl ketone, such as those described for example in International Application PCT/EP2005/008557, which can be followed by conversion of phenol and acetone to bis-phenol-A as described in International Application PCT/EP2005/008554, benzene to phenol and cyclohexanone, or benzene and ethylene to phenol and methyl ethyl ketone, as described for example in International Application PCT/EP2005/008551;

(xviii) in a process of benzene alkylation reactions where selectivity to the monoalkylbenzene is required, e.g., selectively sec-butylbenzene from benzene and $C_4$ olefin feeds that are rich in linear butenes, as described in International Application PCT/EP2005/008557, preferably, this conversion is carried out by co-feeding benzene and the $C_4$ olefin feed with the catalyst of the present invention, at a temperature of about 60° C. to about 260° C., for example of about 100° C. to 200° C., a pressure of 7000 kPa-a or less, and a feed weight hourly space velocity (WHSV) based on $C_4$ alkylating agent of from about 0.1 to 50 h$^{-1}$ and a molar ratio of benzene to $C_4$ alkylating agent from about 1 to about 50; and (xix) in a process for transalkylation, such as, for example, polyalkylbenzene transalkylation.

In the case of many catalysts, it is desired to incorporate the new crystal with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the new crystal, i.e. combined therewith or present during synthesis of the new crystal, which is active, tends to change the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. The materials, i.e. clays, oxides, etc., function as binders for the catalyst. It is desirable to provide a catalyst having good crush strength because in commercial use it is desirable to prevent the catalyst from breaking down into powder-like materials. These clay binders have been employed normally only for the purpose of improving the crush strength of the catalyst.

Naturally occurring clays which can be composited with the new crystal include the montmorillonite and kaolin family, which families include the subbentonites, and the kaolins commonly known as Dixie, McNamee, Georgia and Florida clays or others in which the main mineral constituent is halloysite, kaolinite, dictite, narcite, or anauxite. Such clays can be used in the raw state as originally mined or initially subjected to calcination, treatment or chemical modification. Binders useful for compositing with the present crystal also include inorganic oxides, notably alumina.

In addition to the foregoing materials, the new crystal can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of finely divided EMM-12 crystalline molecular sieve and inorganic oxide matrix vary widely, with the crystal content ranging from about 1 to about 99 percent by weight and more usually, particularly when the composite is prepared in the form of beads, in the range of about 20 to about 80 wt % of the composite.

The following examples reflect embodiments of the invention and are by no means intended to be limiting of the scope of the invention.

Experiments

Powder X-Ray Diffraction

Powder x-ray data were obtained on a Bruker D4 instrument in Bragg-Brentano geometry with monochromatic Cu Kα radiation. The pattern used for structural characterization extended from 1.2 to 80° in 2θ. Intensities for Rietveld refinement were extracted from the continuous scans.

Surface Areas

The overall surface area of a molecular sieve may be measured by the Brunauer-Emmett-Teller (BET) method using adsorption-desorption of nitrogen (temperature of liquid nitrogen, 77 K). The internal surface area may be calculated using t-plot of the Brunauer-Emmett-Teller (BET) measurement. The external surface area is calculated by subtracting the internal surface area from the overall surface area measured by the Brunauer-Emmett-Teller (BET) measurement.

Collidine Number Measurement

The collidine number of a molecular sieve may be measured by TGA. A sample is dried at 200° C. to constant weight (weight change less than ±1% for the period of 1 hour). The weight of the dried sample, the sorbate, is then measured. The sorbent, 2,4,6-collidine, is delivered at 0.3 ml/hr via a gas tight syringe and carried over the sample by nitrogen passed 200 ml/min for 60 min. The collidine number is expressed as micromoles of adsorbed per gram of the sorbate.

NMR Experimental Procedures

All of the solid-state NMR measurements were made at room temperature. The $^{27}$Al and $^{29}$Si MAS NMR spectra were recorded on a Varian InfinityPlus500 spectrometer operating at 11.7 T ($^1$H 499.2 MHz) corresponding to 130 and 99 MHz Larmor frequencies for $^{27}$Al and $^{29}$Si, respectively. $^{29}$Si MAS (Bloch decay) NMR spectra were recorded using a 7.5-mm Varian probe at spinning speeds of 4-kHz, with $^1$H decoupling during data acquisition, 4 μs π/2 pulses, a 60 s pulse delay, and 600 scans were collected. $^{27}$Al MAS (Bloch decay) NMR spectra were recorded using a 4-mm Varian probe at spinning speeds of 10-kHz with $^1$H dipolar decoupling during data acquisition, 1.2 μs π/6 pulses, a 0.3 s pulse delay and 2400-4000 scans were collected. The $^{13}$C CPMAS NMR spectra were recorded using a 5-mm Varian probe at spinning speeds of 4-kHz on a Chemagnetics CMX-200 operating at 4.7 T ($^1$H 199.9 MHz), corresponding to a $^{13}$C Larmor frequency of 50.3 MHz. $^{13}$C CPMAS data were recorded with $^{1}$H decoupling during data acquisition, 3.5 μs π/2 pulses, 3.5 ms contact time, a 2 s pulse delay, and 3200-8000 scans were collected. $^{1}$H MAS NMR spectra were recorded on a 9.4 T Varian InfinityPlus 400 spectrometer corresponding to a $^{1}$H Larmor frequency of 399.4 MHz. $^{1}$H MAS (Bloch decay) data were recorded using a 4-mm Varian probe at spinning speeds of 10-kHz with 4 μs π/2 pulses, a 30 s pulse delay, and 32 scans were collected.

Example 1

A sample of EMM-10-P (1.5 g) made according to Example 1 of U.S. patent application Ser. No. 11/823,129 was added to the mixture of 30 g of 1 M nitric acid and 0.3 g of diethoxydimethylsilane. The reaction was carried out in a teflon container sealed in a Parr™ bomb in the oven at 170° C. for 24 hrs. The solid product was isolated by filtration, washed and dried at 120° C.

Figure 2:
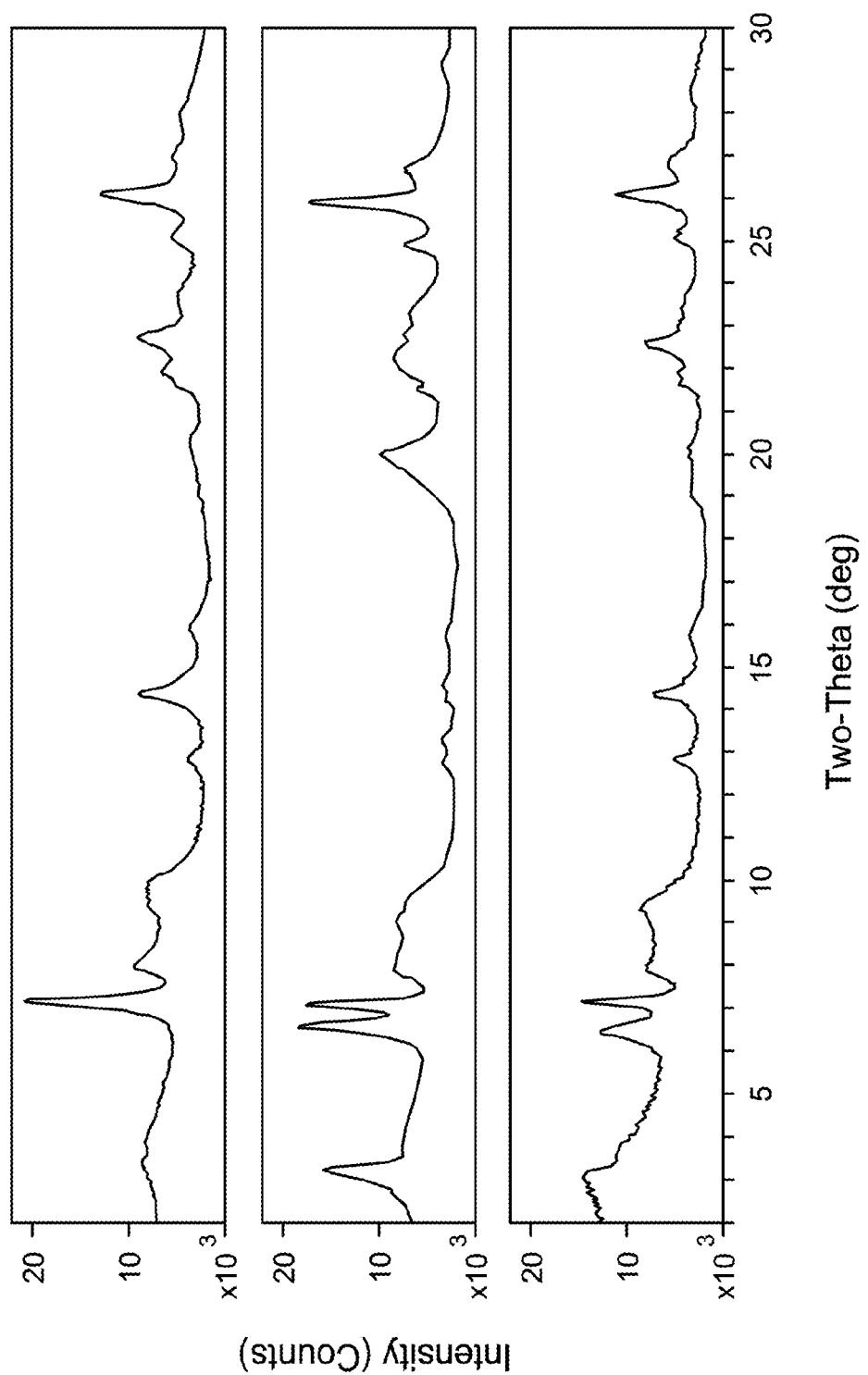
FIG. 2 shows the XRD pattern of the EMM-12 calcined product from Example 1 (bottom), the original EMM-10-P material (middle) and its calcined version without treatment (top).

The XRD pattern (FIG. 2) may be characterized as comprising a doublet at between 12.45 and 13.60 Angstroms, corresponding to 6.5-7.1°2θ (Cu Kα) and non-discrete scattering between 8.85 to 11.05 Angstroms, the 8-10°2θ (Cu Kα) region or exhibit a valley in between the peaks at 11.05±0.18 and 9.31±0.13 Angstroms but with measured intensity corrected for background at the lowest point being not less than 50% of the point at the same XRD d-spacing on the line connecting maxima at around 11.05±0.18 and 9.31±0.13 Angstroms.

The calcined product revealed high surface area of 523 m$^2$/g and extraordinary enhancement of collidine adsorption of 321 μmoles/g.

Not intended to be bound by any theory, we believe that the preservation of the interlayer spacing demonstrated by XRD indicates insertion of an additional thermally stable moiety, most likely incorporating Si atoms. The results of NMR are consistent with this theory.

Figure 3:
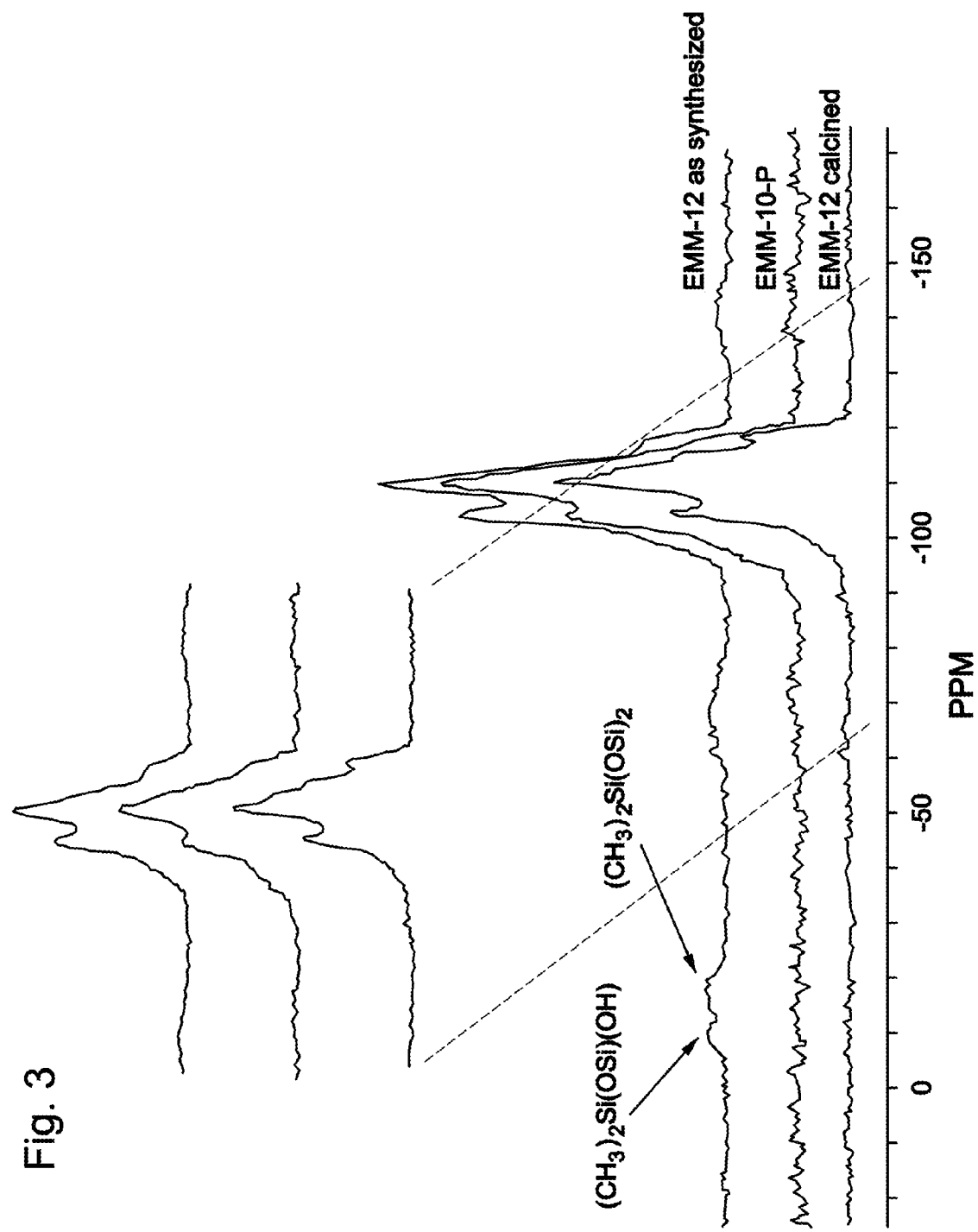
FIG. 3 shows the $^{29}$Si MAS (Bloch decay) NMR spectra of EMM-12 as-synthesized (top), EMM-10-P (middle) and EMM-12 calcined (bottom) for Example 1.
Figure 4:
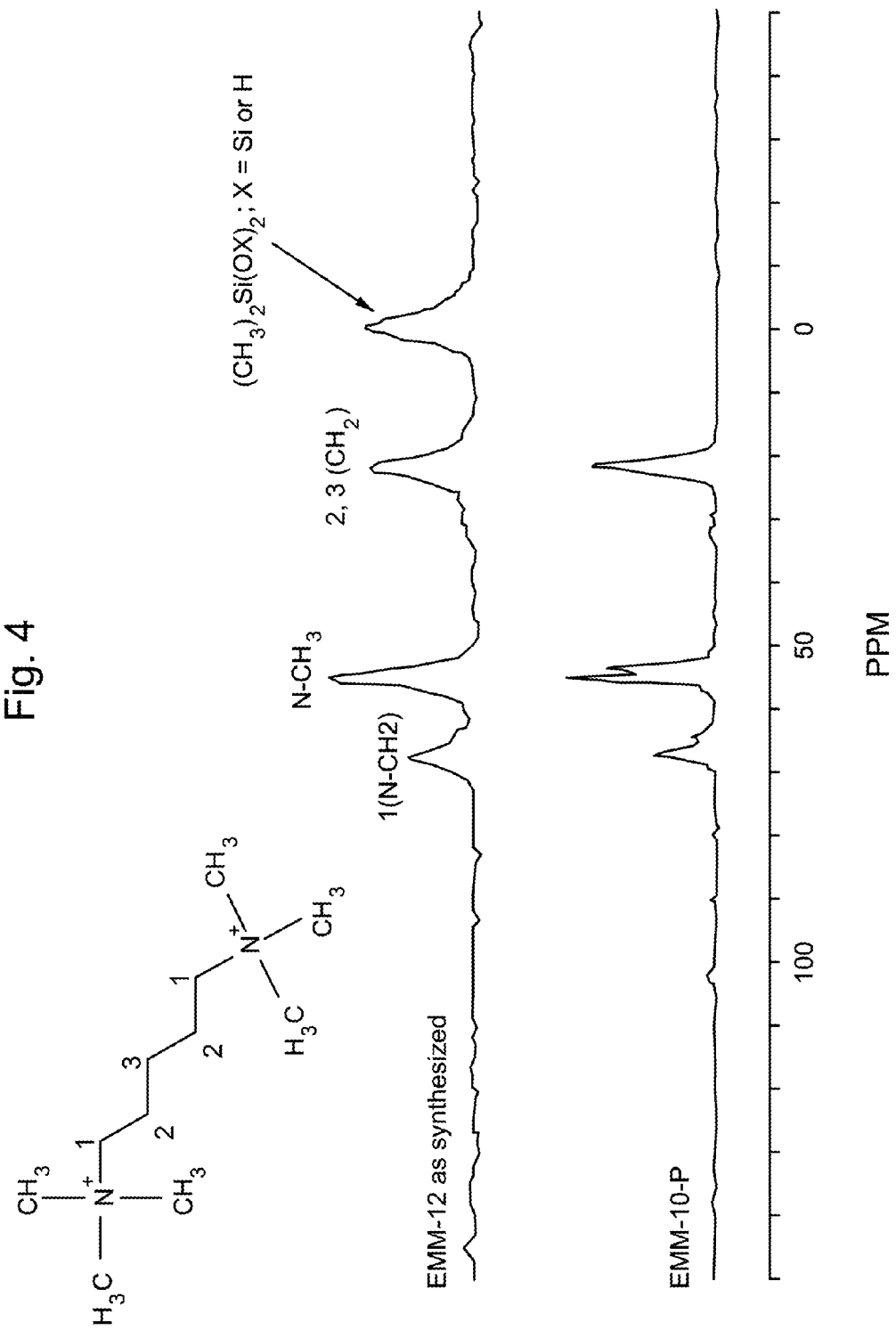
FIG. 4 shows $^{13}$C CPMAS NMR of EMM-10-P (Example 1) and EMM-12 as-synthesized (Example 1).

Shown in FIG. 3 are the $^{29}$Si MAS (Bloch decay) NMR spectra of EMM-12 as-synthesized (top), EMM-10 (middle) and EMM-12 calcined (bottom). Comparison of the spectra of EMM-10 and EMM-12 as-synthesized confirm the reaction of the dimethyldiethoxy silane with the surface to form dimethylsilyl species as indicated by the peaks in the $\delta_{Si}$=−10 to −20 ppm region in EMM-12 as-synthesized. Subsequent calcination of EMM-12 as-synthesized show loss of these peaks, consistent with the loss of the organic functionalities. Close comparison of these spectra, as seen in the inset overlay, show that silylation of EMM-10 to form EMM-12 as-synthesized results in significant loss of intensity in the $\delta_{Si}$=−90 to −102 ppm region which is indicative of loss in silanols due to reaction of the dimethyldiethoxy silane with the surface. Subsequent calcination of the EMM-12 as-synthesized results in an increase in spectral intensity in the $\delta_{Si}$=−110 to −120 ppm region that might be associated with and is consistent with the formation of interlayer Si—O—Si linkages. The presence of surface bound dimethylsilyl species in EMM-12 as-synthesized is also confirmed in the $^{13}$C CPMAS NMR spectrum (FIG. 4) where a resonance associated with methylsilyl is detected ($\delta_C$~0 ppm) in addition to the resonances from the structure directing agent (SDA).

Figure 5:
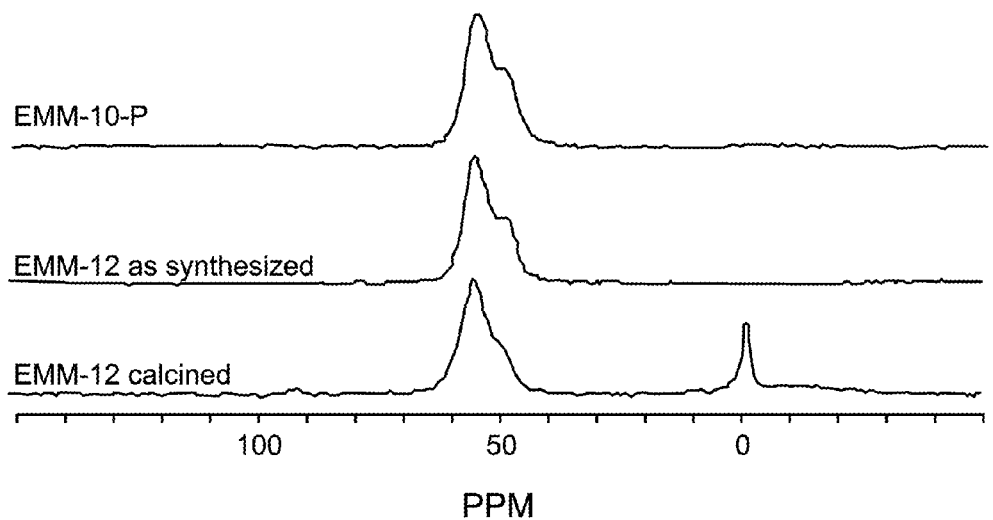
FIG. 5 shows the $^{27}$Al MAS (Bloch decay) NMR spectra of EMM-10-P (top), EMM-12 as-synthesized (middle) and EMM-12 calcined (bottom) for Example 1.

Shown in FIG. 5 are the $^{27}$Al MAS (Bloch decay) NMR spectra of EMM-10-P (top), EMM-12 as-synthesized (middle) and EMM-12 calcined (bottom). Close comparison of these spectra indicate that, perhaps as expected, there is little change in the average local Al tetrahedral environment upon silylation of EMM-10-P. As is typically seen for EMM-10, subsequent calcination of EMM-12 as-synthesized results in the formation of non-framework octahedral Al.

Figure 6:
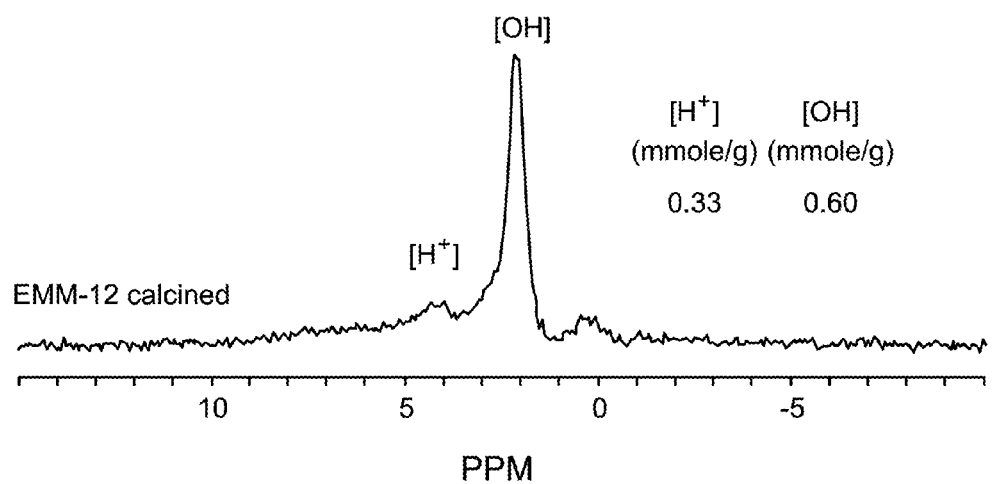
FIG. 6 shows $^1$H MAS NMR spectrum of EMM-12 calcined (Example 1).

The $^{1}$H MAS NMR spectrum of EMM-12 calcined shown in FIG. 6 indicates the presence ~0.33 mmole/g of Brönsted acidity. The SiOH content of 0.60 mmole/g is consistent with what is typically detected in MCM-22/-49 materials.

Example 2

EMM-10-P crystals were synthesized from 123 g of water, 4 g of sodium aluminate solution, 10 g of 50% NaOH, 25 g of Ultrasil and 40 g of the 50% Me6-diquat-5 (Hexamethyl-1, 5-pentanediaminium) bromide solution reacted at 170° C. for 100 hrs. A small amount of EUO zeolite impurity was detected.

Figure 7:
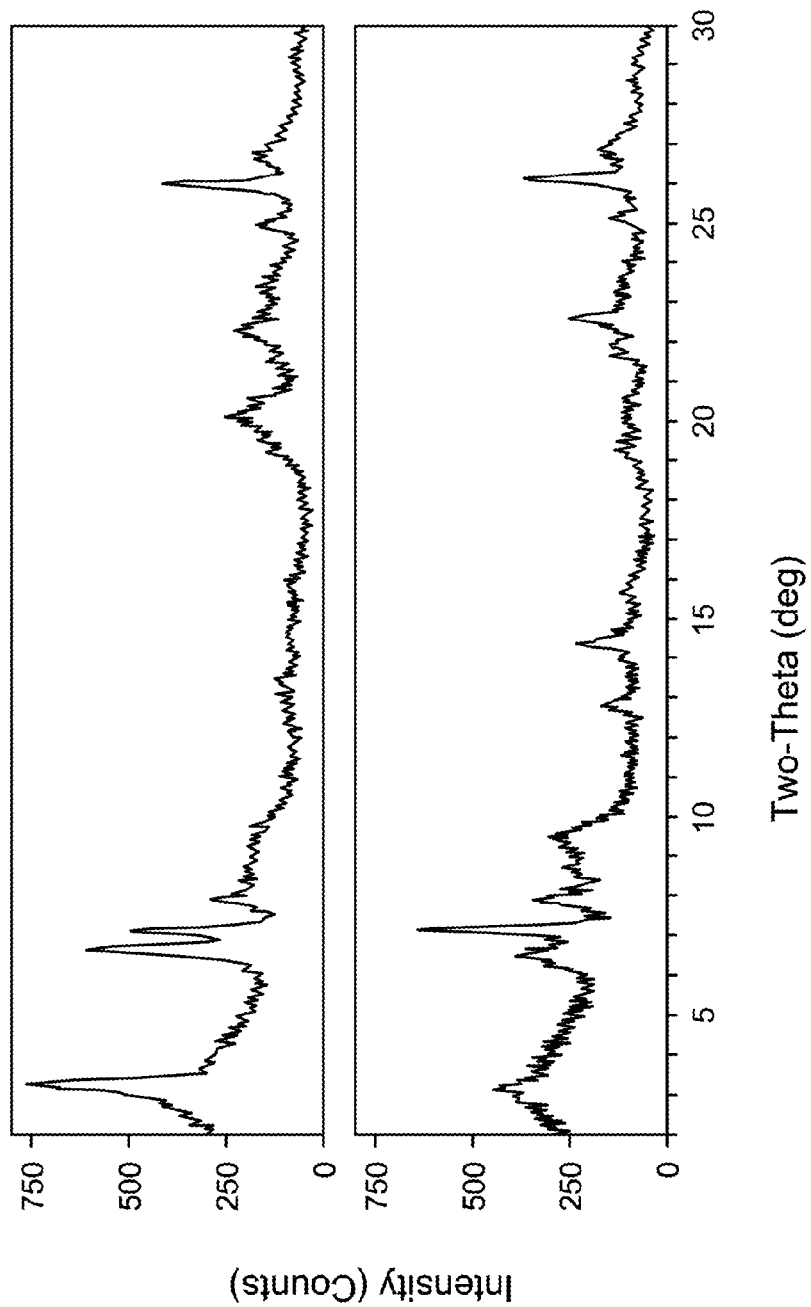
FIG. 7 shows the XRD pattern of the EMM-12 calcined product from Example 2 (bottom) and the original EMM-10-P material (top) of Example 2.

Three grams of the above EMM-10-P was dispersed in 30 g of 1 N nitric acid, and 0.5 g of diethoxydimethylsilane. The mixture was heated for 24 hours at 170° C. yielding 2.92 g of solid. The X-ray diffraction pattern (FIG. 7) contained peaks at 13.5, 12.3, 11.2 and 9.4 Angstroms with a valley between the last two peaks but with measured intensity corrected for background at the lowest point being not less than 50% of the point at the same XRD d-spacing on the line connecting maxima at around 11.2 and 9.4; in addition there was a small peak between the latter two attributed to EUO impurity. The product had in the calcined form BET equal to 574 m$^2$/g, with external surface area 54 m$^2$/g Example 3

A 65 wt. % EMM-12 calcined of Example 1 and 35 wt % alumina catalyst was prepared. This catalyst was tested for benzene alkylation with propylene to form cumene.
Feed Pretreatment
Benzene Benzene was obtained from a commercial source. The benzene was passed through a pretreatment vessel containing equal parts (by volume) molecular sieve 13X, molecular sieve 4A, Engelhard F-24 Clay, and Selexsorb CD (in order from inlet to outlet), and then through a pretreatment vessel containing MCM-22 catalyst. All feed pretreatment materials were dried in a 260° C. oven for 12 hours before using.
Propylene Propylene was obtained from a commercial specialty gases source and was polymer grade.
Nitrogen Nitrogen was ultra high purity grade and obtained from a commercial specialty gases source.
Test Sequence for Cumene Manufacture in a Fixed Bed Test The experiment was conducted in a fixed bed ⅜" or ¾" OD tubular reactor in a downflow configuration with an ⅛" internal thermocouple. The reactor furnace was controlled in isothermal mode. Two grams of catalyst sized to 14/20 mesh was loaded into the ⅜" reactor. Experiment was conducted with catalyst as whole extrudates loaded into the ⅜" reactor. The catalyst bed was axially centered in the middle furnace zone. The catalyst was packed with inert sand to fill the interstitial void spaces. Reaction conditions were 130° C., 2169 kPa-a and the benzene/propylene molar ratio was 3/1. Weight hourly space velocity was 1 hr$^{-1}$ on a propylene basis.

At reactor start-up, the reactor was brought to reaction pressure of 2169 kPa-a with the ultra high purity nitrogen, and heated to reaction temperature of 150° C. prior to introducing the benzene feed for 24 hours. The catalyst was allowed to equilibrate for 1 day prior to introducing the propylene to achieve steady state before data was collected. The reactor was cooled to 130° C. under benzene flow and then propylene was introduced. Products were collected and analyzed for 13 days on-stream. Results shows that Diisopropylbenzene (DIPB) over cumene (isopropylbenzene, IPB) molar ratios of the products fall in the range of 10% to 14%.

We claim:

1. A molecular sieve having, in its as-synthesized form and in its calcined form, an X-ray diffraction pattern including peaks having a d-spacing maximum in the range of 14.17 to 12.57 Angstroms, a d-spacing maximum in the range of 12.1 to 12.56 Angstroms, and non-discrete scattering between about 8.85 to 11.05 Angstroms or exhibit a valley in between the peaks having a d-spacing maximum in the range of 10.14 to 12.0 Angstroms and a d-spacing maximum in the range from 8.66 to 10.13 Angstroms with measured intensity corrected for background at the lowest point being not less than 50% of the point at the same XRD d-spacing on the line connecting maxima in the range of 10.14 to 12.0 Angstroms and in the range from 8.66 to 10.13 Angstroms.

2. The molecular sieve of claim 1, further having, in its as-synthesized form and in its calcined form, an X-ray diffraction pattern including peaks at 3.57±0.07 and 3.42±0.07 Angstroms.

3. The molecular sieve of claim 2, further having, in its as-synthesized form and in its calcined form, an X-ray diffraction pattern including peak at 6.9±0.15 Angstroms.

4. The molecular sieve of claim 1, having a composition involving the molar relationship:

$$X_2O_3:(n)YO_2$$

wherein X is a trivalent element comprises at least one of aluminum, boron, iron and gallium, Y is a tetravalent element comprises at least one of silicon and germanium, and n is at least about 10.

5. The molecular sieve of claim 4, in the as-synthesized form, having a formula, on an anhydrous basis and in terms of moles of oxides per n moles of $YO_2$, as follows:

$$(0.005-1)M_2O:(1-4)R:X_2O_3:nYO_2$$

wherein M is an alkali or alkaline earth metal, and R is an organic moiety.

6. The molecular sieve of claim 4, wherein said n is from about 10 to about 150.

7. The molecular sieve of claim 4, wherein said n is from about 10 to about 50.

8. The molecular sieve of claim 4, wherein X is aluminum and Y is silicon.

9. The molecular sieve of claim 1, having a collidine adsorption capacity of at least 150 µmoles/g.

10. The molecular sieve of claim 1, having a collidine adsorption capacity of at least 250 µmoles/g.

11. A method of manufacturing an as-synthesized crystalline molecular sieve EMM-12, the method comprising the steps of:

(a) providing a mixture comprising EMM-10-P family composition and acidic composition;

(b) treating the mixture under treatment conditions to form a product comprising as-synthesized EMM-12; and (c) recovering the acid treated crystalline molecular sieve.

12. The method of claim 11, wherein said mixture of step (a) further comprising a spacing agent.

13. The method of claim 12, wherein said EMM-10-P family composition comprises EMM-10-P, said acidic composition comprises 1N nitric acid aqueous solution, said spacing agent comprises diethoxydimethylsilane, said treatment conditions comprise a temperature in the range of 90-170° C. and a time in the range of 1 to 24 hours.

14. A method of manufacturing a calcined crystalline molecular sieve EMM-12, the method comprising the step of calcining said as-synthesized crystalline molecular sieve EMM-12 of claim 11 under calcining conditions.

15. A hydrocarbon conversion process comprising the step of contacting a hydrocarbon feedstock with said crystalline molecular sieve EMM-12 of claim 1 under hydrocarbon conversion conditions.

* * * * *

UNITED STATES PATENT AND TRADEMARK OFFICE
CERTIFICATE OF CORRECTION

PATENT NO. : 8,704,025 B2
APPLICATION NO. : 12/999585
DATED : April 22, 2014
INVENTOR(S) : Roth et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 588 days.

Signed and Sealed this
Twenty-ninth Day of September, 2015

Michelle K. Lee
*Director of the United States Patent and Trademark Office*